US00PP36278P2

(12) United States Plant Patent
Heuger

(10) Patent No.: US PP36,278 P2
(45) Date of Patent: Nov. 26, 2024

(54) ***HELLEBORUS* PLANT NAMED 'HON 1612'**

(50) Latin Name: ***Helleborus* x *hybridus* X *Helleborus niger***
Varietal Denomination: HON 1612

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 42 days.

(21) Appl. No.: 18/389,571

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

*Primary Examiner* — Karen M Redden
(74) *Attorney, Agent, or Firm* — C. Anne Whealy

(57) ABSTRACT

A new and distinct cultivar of *Helleborus* plant named 'HON 1612', characterized by its upright to somewhat outwardly spreading and mounded plant habit; moderately vigorous growth habit; dark green-colored leaflets with lighter green-colored venation; freely flowering habit; purplish red-colored flowers; and good garden performance.

1 Drawing Sheet

Figure 1:
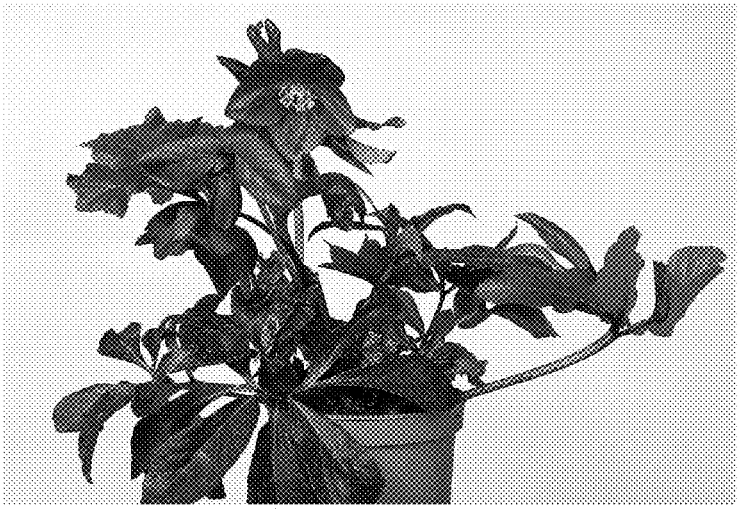

Botanical designation: *Helleborus* x *hybridus* X *Helleborus niger.*
Cultivar denomination: 'HON 1612'.

CROSS-REFERENCED TO CLOSELY-RELATED APPLICATIONS

Title: *Helleborus* Plant Named 'HON 1610'
Inventor/Applicant: Josef Heuger
application Ser. No. 18/389,569
Filed: Concurrently with the instant application

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1380. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *hybridus* X *Helleborus niger* and hereinafter referred to by the name 'HON 1612'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November, 2013 of a proprietary selection of *Helleborus* x *hybridus* identified as code number 01689, not patented, as the female, or seed, parent and a proprietary selection of *Helleborus* x *hybridus* identified as code number 01412, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2015.

Asexual reproduction of the new *Helleborus* plant by in vitro axillary meristem culture in a controlled environment in Glandorf, Germany since April, 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HON 1612'. These characteristics in combination distinguish 'HON 1612' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.
5. Purplish red-colored flowers.
6. Good garden performance.

Plants of the new *Helleborus* differ from plants of the female parent selection in the following characteristics:

1. Plants of the new *Helleborus* have larger flowers than plants of the female parent selection.
2. Flowers of plants of the new *Helleborus* are purplish red in color whereas flowers of plants of the female parent selection are white in color.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are purplish red in color whereas flowers of plants of the male parent selection are red in color.

Plants of the new *Helleborus* can be compared to plants of *Helleborus* x *hybridus* X *Helleborus niger* 'HON 1610', disclosed in a U.S. Plant patent application Ser. No. 18/389,569. In side-by-side comparisons, plants of the new *Helleborus* differ primarily from plants of 'HON 1610' in flower color as plants of the new *Helleborus* have purplish red-colored flowers whereas plants of 'HON 1610' have purplish pink-colored flowers.

Plants of the new *Helleborus* can also be compared to plants of *Helleborus orientalis* 'HLR 180', disclosed in U.S. Plant Pat. No. 22,020. In side-by-side comparisons, plants of the new *Helleborus* differ primarily from plants of 'HLR 180' in flower color as plants of the new *Helleborus* have purplish red-colored flowers whereas plants of 'HLR 180' have white-colored flowers with red purple-colored spots.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HON 1612' grown in a container.

Figure 2:
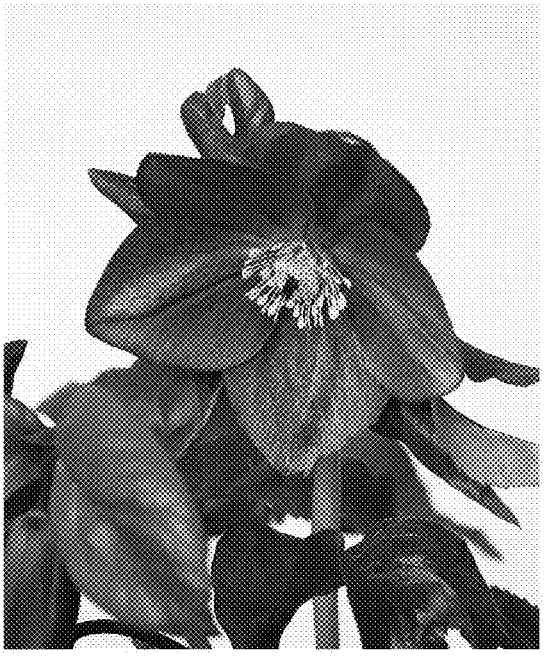

The photograph at the bottom of the sheet (FIG. 2) is a close-up view of a typical flowering plant of 'HON 1612'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus* x *hybridus* X *Helleborus* x *hybridus* 'HON 1612'.

Parentage:

*Female, or seed, parent*.—Proprietary selection of *Helleborus* x *hybridus* identified as code number 01689, not patented.

*Male, or pollen, parent*.—Proprietary selection of *Helleborus niger* identified as code number 01412, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within to slightly above the foliar plane; plant shape, roughly flattened globular; moderately vigorous growth habit and moderate growth rate.

*Plant height, soil level to top of foliar plane*.—About 25.8 cm.

*Plant height, soil level to top of flowers*.—About 26.6 cm.

*Plant diameter* (*area of spread*).—About 45.9 cm.

Leaf description:

*Arrangement*.—Leaves arranged in a basal rosette; leaves palmately compound with typically five to seven leaflets per leaf.

*Leaf length*.—About 21.5 cm.

*Leaf width*.—About 23.4 cm.

*Leaflet length*.—About 12.6 cm.

*Leaflet width*.—About 6.9 cm.

*Leaf shape*.—Palmate; roughly reniform in outline.

*Leaflet shape*.—Elliptic to obovate.

*Leaflet apex*.—Acute.

*Leaflet base*.—Attenuate.

*Leaflet margin*.—Serrate; moderately coarsely undulate.

*Leaflet texture and luster, upper and lower surfaces*.—Smooth, glabrous; coriaceous and tough; moderately glossy.

*Leaflet venation pattern*.—Pinnate and reticulate.

*Leaflet color*.—Developing leaflets, upper surface: Close to 143A; at the base, close to 183A and 187A. Developing leaflets, lower surface: Close to a blend of 144A and 146B; marginal edges, close to N186C; venation, close to 178B. Fully developed leaflets, upper surface: Close to a blend of NN137A and 147A; towards the base, tinged with close to 200A; venation, close to 144B. Fully developed leaflets, lower surface: Close to 147B; venation, close to 145A.

*Petioles*.—Length: About 17.9 cm. Diameter: About 7 mm by 8 mm. Strength: Strong. Texture and luster, upper and lower surfaces: Smooth, glabrous; moderately glossy. Color, upper surface: Close to 146C; moderately to densely covered with fine dots, close to N186C; proximally, heavily covered with fine dots, close to 187A. Color, lower surface: Close to 146C; heavily covered with fine dots, close to 187A and 187B.

Flower description:

*Flower shape and habit*.—Single rotate bowl-shaped flowers arranged in panicles; freely flowering habit with about four flowers per inflorescence and about 16 flowers and flower buds per plant; flowers are slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.3 cm. Diameter: About 1.3 cm. Shape: Ovate. Texture and luster: Smooth, glabrous; matte. Color: Close to 71A; towards the base, close to 150D.

*Inflorescence height* (*including peduncle*).—About 27.5 cm.

*Inflorescence diameter*.—About 15.6 cm.

*Flower diameter*.—About 11.3 cm.

*Flower depth*.—About 3 cm.

*Petals*.—All petals are transformed into nectaries.

*Sepals*.—Quantity and arrangement: About five, arranged in a single whorl. Length: About 6.1 cm. Width: About 5.2 cm. Shape: Broadly ovate to close to rhomboidal; slightly concave. Apex: Broadly and bluntly acute. Base: Broadly attenuate to cuneate. Margin: Entire; slightly coarsely undulate. Texture and luster, upper surface: Smooth, glabrous; matte. Texture and luster, lower surface: Smooth, glabrous; slightly glossy. Color: When opening, upper surface: Close to 71A; towards the margins and apex, close to 70A. When opening, lower surface: Close to a blend of 71A and N186D; center, close to 70A. Fully opened, upper surface: Close to 71A to close to a blend of 71A and N186D; towards the base, close to 151C; venation, similar to lamina color; color does not change with subsequent development. Fully opened, lower surface: Slightly darker than close to 64A; venation, similar to lamina colors; color does not change with subsequent development.

*Flower bracts*.—Quantity per flower: Typically one. Length: About 10.4 cm. Width: About 7.5 cm. Shape: Ovate/oblong to obovate. Apex: Acute to two or three-parted. Base: Truncate to cuneate. Margin: Proximally, entire, and distally, serrate; coarsely undulate. Color, upper surface: Close to NN137B; towards the base, close to 145A to 145B; midvein, occasionally tinged with close to 187A to 187C. Color, lower surface: Close to 147B; midvein, close to 187B.

*Peduncles*.—Length: About 22.8 cm. Diameter: About 7.5 mm to 8 mm. Aspect: About 10 degrees from vertical. Strength: Strong. Texture and luster: Smooth, glabrous; moderately glossy. Color: Close to 146D; sparsely to heavily covered with fine dots, close to 187B.

*Pedicels*.—Length: About 5.1 cm. Diameter: About 3 mm. Aspect: About 30 degrees from peduncle axis. Strength: Moderately strong. Texture and luster: Smooth, glabrous; slightly glossy. Color: Close to 146D; moderately covered with fine dots, close to 183A.

*Reproductive organs*.—Stamens: Quantity per flower: About 120. Filament length: About 1.5 cm. Filament color: Close to 155A. Anther shape: Double and broadly reniform; basifixed. Anther size: About 2 mm by 3 mm. Anther color: Close to 154D. Pollen amount: Sparse to moderate. Pollen color: Close to 4D to lighter than 4D. Pistils: Quantity per flower: About five to seven. Pistil length: About 1.1 cm. Stigma diameter: About 0.3 mm. Stigma shape: Club-shaped. Stigma color: Close to 156D. Style length: About 1.05 mm. Style color: Close to N186C; proximally, close to 183C. Ovary color: Close to 151B; adaxial rib, close to 183C to 183D. Nectaries (transformed petals): Quantity per flower: About 13. Length: About 1.1 cm. Diameter: About 5 mm. Shape: Tubular, flattened; apices, obtuse. Texture and luster, inner and outer surfaces: Smooth, glabrous; slightly glossy. Color, immature, inner and outer surfaces: Close to 144B; at the base, close to 152C.

Color, mature, inner and outer surfaces: Close to N144C; distally, close to N144D; at the base, close to 152C; venation, similar to lamina colors; with subsequent development, color becoming closer to N144B, distally, close to 151C and at the base, close to 152C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HON 1612' as illustrated and described.

* * * * *